(12) United States Patent
Konno et al.

(10) Patent No.: US 7,570,735 B2
(45) Date of Patent: Aug. 4, 2009

(54) X-RAY CT SCANNER

(75) Inventors: Yasutaka Konno, Saitama (JP); Osamu Miyazaki, Moriya (JP)

(73) Assignee: Hitachi Medical Corporation, Tokyo (JP)

( * ) Notice: Subject to any disclaimer, the term of this patent is extended or adjusted under 35 U.S.C. 154(b) by 223 days.

(21) Appl. No.: 10/587,171

(22) PCT Filed: Jan. 17, 2005

(86) PCT No.: PCT/JP2005/000459

§ 371 (c)(1),
(2), (4) Date: Jun. 1, 2007

(87) PCT Pub. No.: WO2005/102172

PCT Pub. Date: Nov. 3, 2005

(65) Prior Publication Data

US 2007/0297562 A1    Dec. 27, 2007

(30) Foreign Application Priority Data

Apr. 23, 2004   (JP)   ............................. 2004-128137

(51) Int. Cl.
*A61B 6/03* (2006.01)
(52) U.S. Cl. ........................................ 378/19; 378/207
(58) Field of Classification Search ................ 378/4, 378/19, 98.7, 98.8, 207
See application file for complete search history.

(56) References Cited

U.S. PATENT DOCUMENTS

| 5,265,013 | A | | 11/1993 | King et al. |
| 5,359,638 | A | | 10/1994 | Hsieh et al. |
| 5,452,338 | A | * | 9/1995 | Granfors et al. ............. 378/207 |
| 5,644,610 | A | * | 7/1997 | Crawford et al. ............. 378/19 |
| 2004/0267507 | A1 | * | 12/2004 | Stierstorfer .................. 378/19 |
| 2005/0036582 | A1 | * | 2/2005 | Nagaoka et al. ............... 378/19 |

FOREIGN PATENT DOCUMENTS

| JP | 06-343629 | 12/1994 |
| JP | 09-248300 | 9/1997 |
| JP | 2001-309915 | 11/2001 |
| JP | 2003-061945 | 3/2003 |

* cited by examiner

*Primary Examiner*—Chih-Cheng G Kao
(74) *Attorney, Agent, or Firm*—Antonelli, Terry, Stout & Kraus, LLP.

(57) ABSTRACT

An X-ray CT scanner characterized in that it comprises first storage means for storing data on the response characteristic of an X-ray detector measured previously and representing the characteristic of the afterglow and second storage means for storing output data of the X-ray detector on the past projections corrected by correcting means by using the data on the response characteristic and in that the correcting means has afterglow correcting means for correcting the influence of inflow of signal from the past projections due to the afterglow on the output data on the present projection and the influence of outflow of signal on the future projections by using the data on the response characteristic stored in the first storage means and the past output data stored in the second storage means on the projections.

7 Claims, 9 Drawing Sheets

IMAGE WITHOUT
AFTERGLOW CORRECTION

FIG.9B

IMAGE WITH
AFTERGLOW CORRECTION

X-RAY CT SCANNER

TECHNICAL FIELD

The present invention relates to an X-ray CT scanner.

BACKGROUND ART

Solid-state detectors that are highly sensitive and can be designed compactly are becoming mainstream detectors to be included in X-ray CT scanners. The structure includes a plurality of X-ray detecting elements each of which is a combination of a scintillator that convert an X-ray into light and a photodiode that converts light into an electric signal, and an electric readout circuit that reads the electric signals. The solid-state detector causes a phenomenon (afterglow) that an image formed during previous projection remains in projection data items produced during subsequent projections because of both afterglow occurring when the scintillators convert X-rays into light and signals left unread by the readout circuit.

When X-rays are irradiated, if afterglow does not occur, all signals induced by X-rays can be used to produce projection data during immediately succeeding projection (current projection). However, if afterglow occurs, all the signals cannot be used during projection immediately succeeding X-ray irradiation. Part of the signals remains over a plurality of subsequent projections. Consequently, during the projections, the signals having remained since past projections are added to signals originally acquired during current projection. This results in artifacts. The artifacts contained in projection data deteriorate image quality of reconstructed images and degrade a time resolution.

The afterglow includes a plurality of different components. This is because when the scintillator glows, the time constant of emitted light varies depending on which of a plurality of physical processes is followed from the instant the scintillator loses X-ray energy to the instant it glows. Besides, the readout circuit leaves some signals unread. Consequently, generally, afterglow is defined as the sum of components exhibiting different time constants.

Various methods have been proposed as a correction method of removing afterglow composed of a plurality of components. Proposed as one of the methods in Japanese Patent Application Laid-Open No. 6-343629 is such that a measured afterglow amount is subtracted from the result of convolution integral of the response characteristic of an X-ray detector and corrected output data items in order to compensate an adverse effect of the afterglow components occurring during respective past projections.

DISCLOSURE OF THE INVENTION

Problem to be Solved by the Invention

An adverse effect of afterglow on current projection includes inflow of signals left unread during past projections, and outflow of signals left unread during current projection to future projections.

Consequently, not only signals to be added because they have remained since past projections but also signals to be added to signals that will be induced during future projections are corrected in order to highly precisely reproduce the true signals induced during current projection. Degradation in a spatial resolution of a reconstructed image derived from afterglow, and deterioration in image quality derived from artifacts should thus be prevented.

An object of the present invention is to provide an X-ray CT scanner capable of minimizing or removing artifacts in an image derived from afterglow caused by a detector, and highly precisely preventing degradation in a time resolution by performing correction.

Means for Solving the Problem

In order to accomplish the above object, an X-ray CT scanner in accordance with the present invention has features described below.

(1) An X-ray CT scanner includes: an X-ray source that irradiates X-rays to an object; an X-ray detector that includes a plurality of X-ray detecting elements which convert X-rays penetrating the object into electric signals at every timing of projection; a data correction means for correcting an output of the X-ray detector; and an arithmetic processing means for performing arithmetic processing on an output of the data correction means so as to reconstruct an image. The X-ray CT scanner further includes a first memory means in which data of the response characteristic of the X-ray detector that is the afterglow-related characteristic thereof and that is measured in advance is stored, and a second memory means in which output data items produced by the X-ray detector during past projections and corrected by the data correction means on the basis of the response characteristic data is stored. The data correction means includes an afterglow correction means that uses both the response characteristic data stored in the first memory means, and a plurality of output data items which are produced during a plurality of past projections and stored in the second memory means to compensate both an adverse effect of inflow of signals from past projections, which is derived from the afterglow, on output data produced during current projection and an adverse effect of outflow of signals to future projections.

(2) An X-ray CT scanner includes: an X-ray source that irradiates X-rays to an object; an X-ray detector that includes a plurality of X-ray detecting elements which convert X-rays penetrating the object into electric signals at every timing of projection; a data correction means for correcting an output of the X-ray detector; and an arithmetic processing means for performing arithmetic processing on an output of the data correction means so as to reconstruct an image. The X-ray CT scanner further includes a first memory means in which data of the response characteristic of the X-ray detector that is the afterglow-related characteristic thereof and that is measured in advance is stored, and a second memory means in which output data items produced by the X-ray detector during past projections and corrected by the data correction means on the basis of the response characteristic data are stored. The data correction means includes an afterglow correction means that uses both the response characteristic data stored in the first memory means and the output data items produced during past projections and stored in the second memory means to compensate both an adverse effect of inflow of signals from the past projections, which is derived from afterglow, on output data produced during current projection and an adverse effect of outflow of signals to future projections according to a predetermined expression. Assuming that Lag (j) denotes the ratio of afterglow components having occurred over j projections since the irradiated X-rays fall on the X-ray detector, m denotes the number of past projections over which afterglow components to be compensated have occurred since the X-rays fall on the X-ray detector, n denotes the number of future projections for which an afterglow component having occurred since the X-rays fall on the X-ray detector should be compensated, I(N) denotes output data acquired when N projections have been completed since the X-rays fall on the X-ray detector, and I'(N) denotes output data produced when the data correction means has corrected the output data I(N) acquired after completion of N projections and affected by afterglow, an expression is provided as follows:

$$I'(N) = \frac{I(N) - \sum_{j=1}^{m}(Lag(j) \cdot I'(N-j))}{1 - \sum_{j=1}^{n}(Lag(j))}$$ [Expression 1]

The expression is adopted as the predetermined expression.

Owing to the X-ray CT scanner, both an adverse effect of inflow of signals from past projections and an adverse effect of outflow of signals to future projections are compensated in order to highly precisely reproduce true signals produced during current projection. Consequently, degradation in a spatial resolution of a reconstructed image derived from afterglow and deterioration in image quality derived from occurrence of artifacts can be prevented.

(3) In the X-ray CT scanner mentioned in (2), the response characteristic of the X-ray detector is indicated by the sum of afterglow components which exhibit different time constants and intensities. The number of past projections, m, over which afterglow components to be compensated have occurred, and/or the number of future projections, n, for which an afterglow component having occurred since the X-rays fall on the X-ray detector should be compensated vary depending on an afterglow component.

Consequently, the number of calculations to be performed during afterglow correction is decreased.

(4) An X-ray CT scanner includes an X-ray source that irradiates X-rays to an object, an X-ray detector that includes a plurality of X-ray detecting elements which convert X-rays penetrating the object into electric signals, a data correction means for correcting an output of the X-ray detector, and an arithmetic processing means for performing arithmetic processing on an output of the data correction means so as to reconstruct an image. The X-ray CT scanner further includes a first memory means in which time constants and intensities of respective afterglow components determined in advance are stored, and a second memory means in which output data items produced by the X-ray detector during past projections and corrected by the data correction means on the basis of the time constants and intensities of the respective afterglow components. The data correction means includes an afterglow correction means that uses both the time constants and intensities of the respective afterglow components stored in the first memory means and the output data items produced during the past projections and stored in the second memory means to compensate, according to a predetermined expression, both an adverse effect of inflow of signals from the past projections, which is derived from afterglow, on output data produced during current projection, and an adverse effect of outflow of signals to future projections. Assuming that $\Delta T$ denotes a time interval between projections, M denotes the number of afterglow components, $\tau_i$ denotes a time constant of an afterglow component i (where i denotes 1, 2, etc., or M), $A_i$ denotes an intensity of the afterglow component i, $m_i$ denotes the number of past projections over which afterglow components i to be compensated have occurred since the X-rays fall on the X-ray detector, $n_i$ denotes the number of future projections for which an afterglow component i having occurred since the X-rays fall on the X-ray detector should be compensated, I(N) denotes output data acquired when N projections have been completed since the X-rays fall on the X-ray detector, and I'(N) denotes output data produced when the data correction means corrects the output data I(N) acquired after the completion of N projections so as to compensate the afterglow, an expression is provided as follows:

$$I'(N) = \frac{I(N) - \sum_{i=1}^{M}\left(\sum_{j=1}^{mi}\left(A_i \exp\left(-\frac{j\Delta T}{\tau_i}\right) \cdot I'(N-j)\right)\right)}{1 - \sum_{i=1}^{M}\left(\sum_{j=1}^{ni}\left(A_i \exp\left(-\frac{j\Delta T}{\tau_i}\right)\right)\right)}$$ [Expression 2]

The expression is adopted as the predetermined expression.

Consequently, an amount of response characteristic data to be stored in the first memory means is minimized, and the number of calculations to be performed for afterglow correction is decreased.

(5) The X-ray CT system mentioned in (1), (2), or (4) supports an afterglow measurement mode in which the X-rays are impulsively irradiated only during a projection or stepwise irradiated only during a plurality of projections in order to acquire in advance data of the response characteristic of the X-ray detector that is the afterglow-related characteristic thereof, and includes a facility for selecting the afterglow measurement mode.

Consequently, the afterglow-related characteristic that is the response characteristic of the X-ray detector can be measured.

According to the present invention, there is provided an X-ray CT scanner capable of minimizing or removing artifacts in an image derived from afterglow caused by a detector or highly precisely preventing degradation in a time resolution by performing correction.

BEST MODE FOR CARRYING OUT THE INVENTION

Referring to the drawings, embodiments of the present invention will be described below.

First Embodiment

Referring to FIG. 1 to FIG. 5, the first embodiment of the present invention will be described below.

Figure 1:
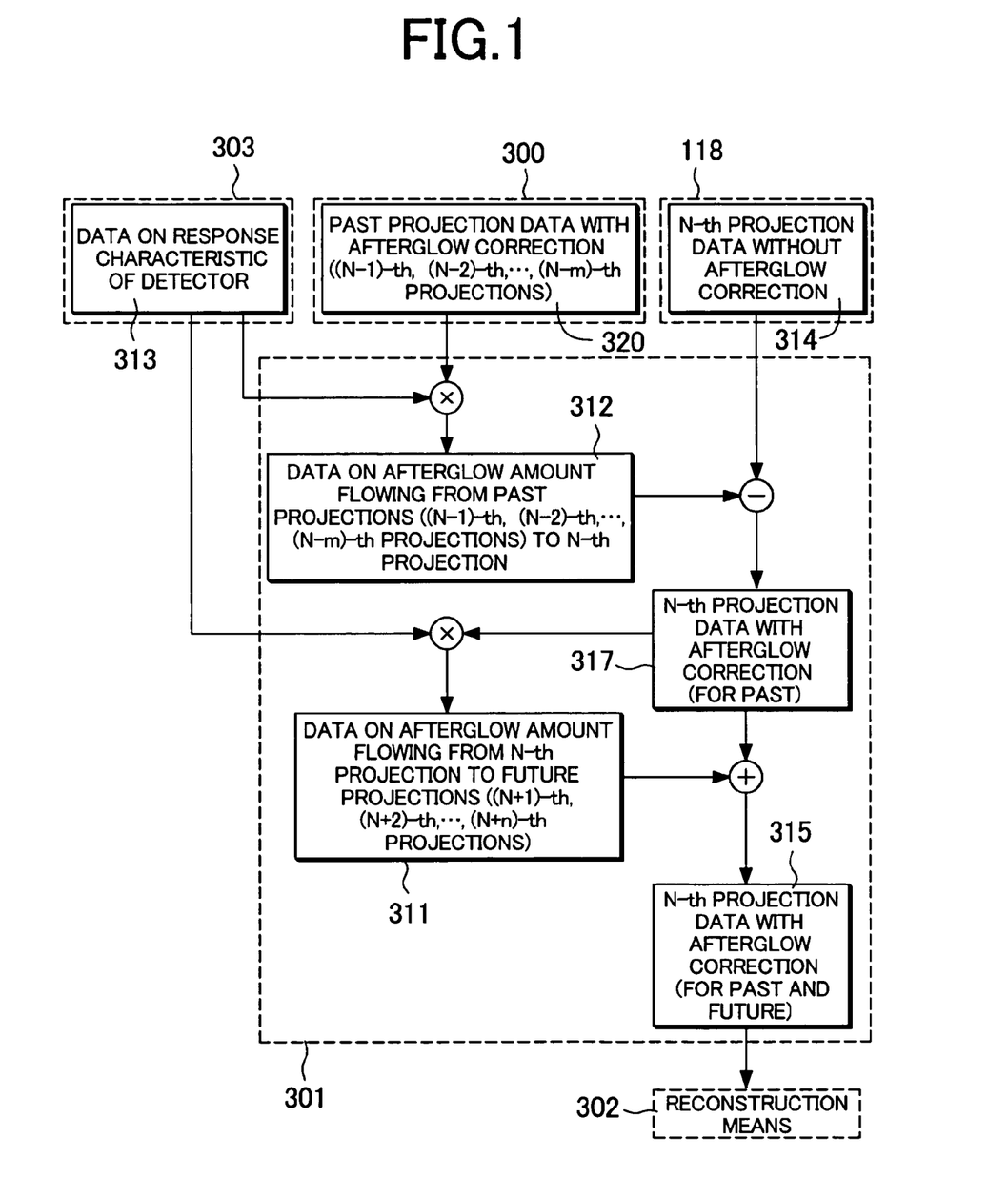
FIG. 1 is an explanatory diagram concerning an example of an afterglow correction method to be implemented by a data correction means included in the first embodiment of the present invention (first embodiment)
Figure 2:
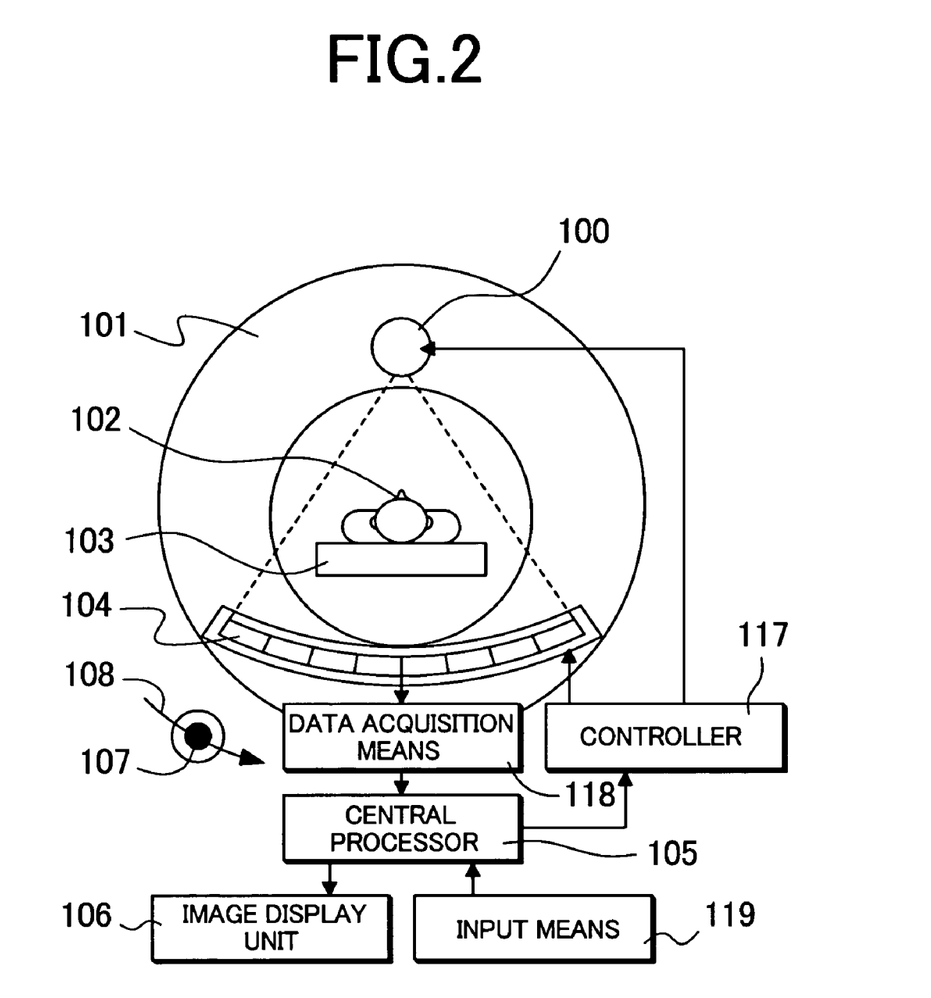
FIG. 2 shows an embodiment of an X-ray CT scanner in accordance with the present invention including an afterglow correction means (first embodiment)
Figure 3:
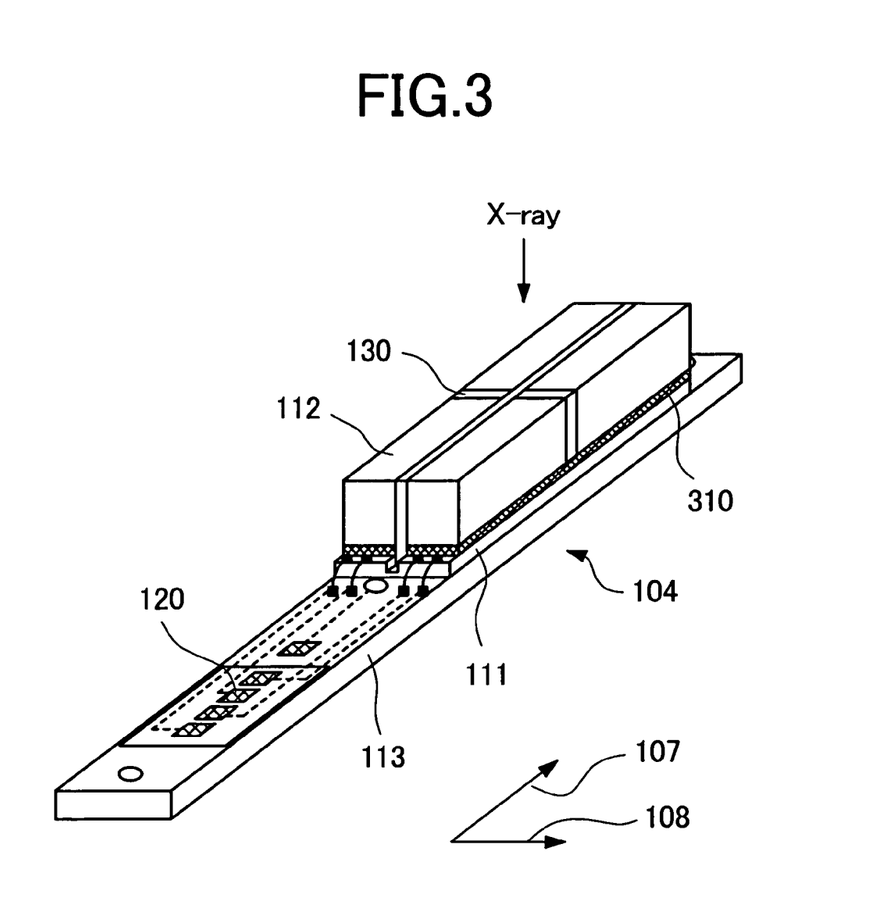
FIG. 3 is an explanatory diagram showing an example of the configuration of an X-ray detector shown in FIG. 2 (first embodiment)
Figure 4:
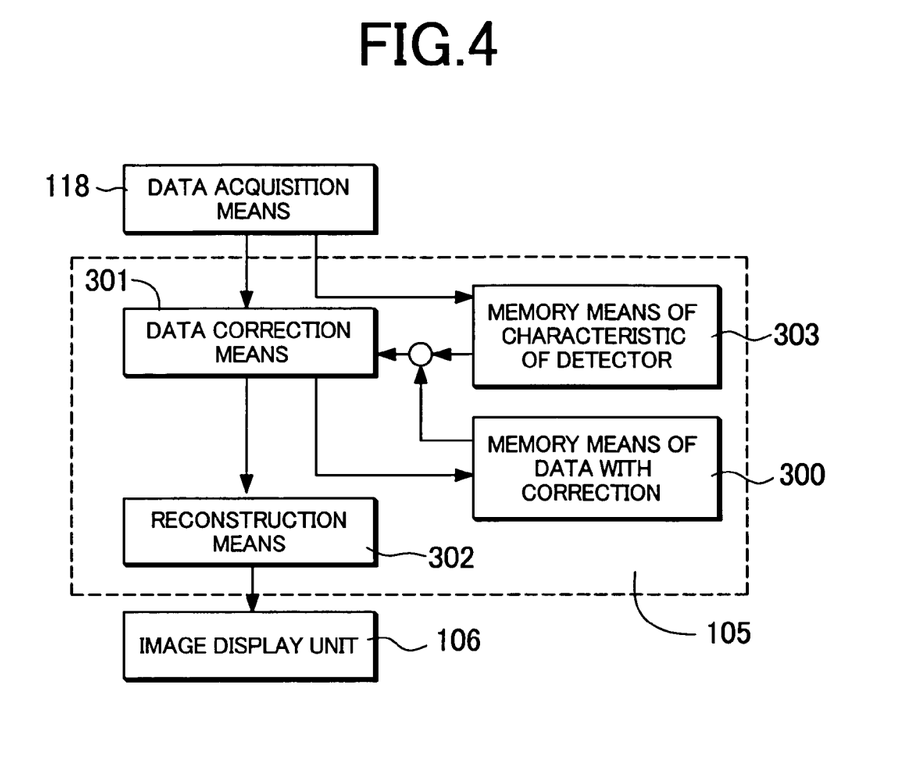
FIG. 4 is an explanatory diagram describing an example of processing to be performed by a central processor shown in FIG. 2 (first embodiment)
Figure 5:
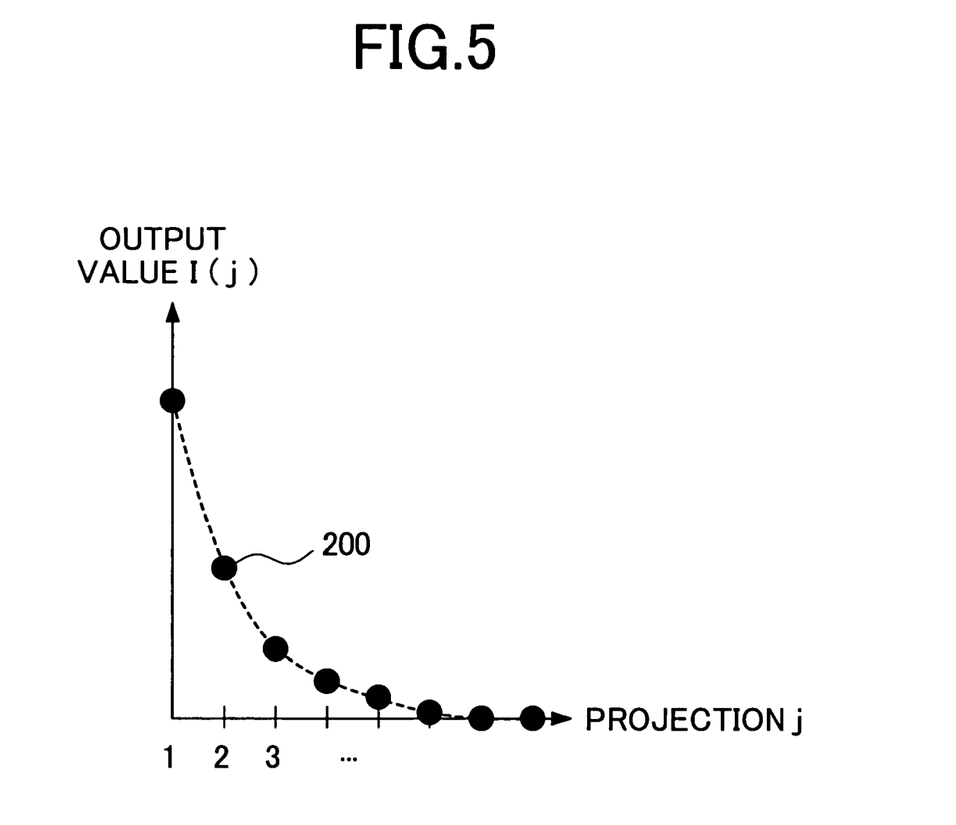
FIG. 5 is an explanatory diagram concerning the ratio Lag(j) (j denotes the number of projections to be completed after X-ray irradiation) of afterglow components calculated based on data of the response characteristic of a detector shown in FIG. 1 (first embodiment)

FIG. 2 shows an embodiment of an X-ray CT scanner in accordance with the present invention including an afterglow correction means. FIG. 3 is an explanatory diagram showing an example of the configuration of an X-ray detector included in the X-ray CT scanner shown in FIG. 2. FIG. 4 is an explanatory diagram showing an example of the configuration of a central processor included in the X-ray CT scanner shown in FIG. 2. FIG. 1 is an explanatory diagram concerning an example of an afterglow correction method to be implemented by a data correction means shown in FIG. 4. FIG. 5 is an explanatory diagram concerning the ratio Lag(j) (j denotes the number of projections completed after X-ray irradiation) of afterglow components calculated based on data 313 of the response characteristic of a detector shown in FIG. 1.

As shown in FIG. 2, the basic components of the X-ray CT scanner include an X-ray tube 100 that irradiates X-rays, an X-ray detector 104 that detects X-rays and converts them into electric signals, a data acquisition means 118 that acquires projection data produced by the X-ray detector 104, a central processor 105 that stores signals (projection data) sent from the data acquisition means 118 and performs image processing, an image display unit 106 that displays the results of image processing, an input means 119 that initiates imaging and designates or receives parameters, and a controller 117 that controls the X-ray tube 100 and X-ray detector 104. In the drawing, reference numeral 107 denotes a body-axis direction (slicing direction), and reference numeral 108 denotes a rotating direction (direction of channels) of a rotated gantry 101.

Referring to FIG. 2, an imaging procedure will be described below. When initiation of imaging is entered at the input means 119, X-rays are irradiated from the X-ray source 100 to an object 102 lying down on a bed 103. The X-rays penetrating the object 102 are converted into electric signals by the X-ray detector 104. The electric signals are analog-to-digital converted by the data acquisition means 118 and provided as projection data. The imaging is repeatedly performed for each projection by rotating the rotated gantry 101, which accommodates the X-ray tube 100 and X-ray detector 104, and changing an X-ray irradiation angle with respect to the object. Consequently, projection data items are acquired over 360°. The imaging is performed at intervals of, for example, 0.4° in order to produce projection data during each projection. At this time, the controller 117 controls rotation of the rotated gantry 101 and reading by the X-ray detector 104. The central processor 105 performs image correction or reconstruction on the projection data. The result is displayed on the image display unit 106.

Referring to FIG. 3, an example of the configuration of the X-ray detector 104 included in the X-ray CT scanner in accordance with the present invention will be described below. A plurality of X-ray detectors 104 one of which is shown in FIG. 3 are arranged in the form of an arc, and opposed to the X-ray tube 100 as shown in FIG. 2. The X-ray detector 104 shown in FIG. 3 includes a photodiode module (photoelectric module) 111 having a plurality of scintillators 112, which convert X-rays into light, and a plurality of photodiodes, which convert light into electric signals, formed thereon, electrode pads 120 that transmit the electric signals, and a distribution module 113 in which wiring is patterned. Each of the scintillators 112 is bonded to the photodiode module 111 using an optically transparent bonding agent 310, whereby an X-ray detecting element is constructed. The scintillators are borne by the photodiode module 111. Herein, the number of X-ray detecting elements included in the X-ray detector 104 shown in FIG. 3 is provided for brevity's sake but does not restrict the present invention.

Referring to FIG. 3, incidence of X-rays on the X-ray detector 104 will be described below. Incident X-rays are converted into light by the scintillators 112. The scintillators 112 are separated from one another by a separator 130. The photodiode opposed to each of the scintillators 112 in order to convert light into an electric signal is mounted on the photodiode module 111. The photodiode and scintillator 112 constitute an X-ray detecting element. An electric signal into which light is converted by the photodiode is transmitted from each X-ray detecting element. The electrode of the photodiode is electrically coupled to the electric pad 120. The electric signal induced by an X-ray is read from the electrode pad 120 by the data acquisition means 118 shown in FIG. 2. The electric signals produced by all the X-ray detecting elements are collected to produce projection data. A plurality of projection data items are sequentially produced at intervals of a certain time ($\Delta T$). The N-th projection data may be called N-th-projection projection data, projection data of the N-th projection, or projection data produced during the N-th projection.

During reading, all signals induced by X-rays are not read during projection immediately succeeding X-ray irradiation. Afterglow causes outflow of some signals to another projection. For example, part of signals induced by X-rays irradiated immediately before (N−1)-th-projection projection data is produced is not read until N-th-projection projection data is produced. This attributes to a delay (afterglow) in conversion from X-rays to light by the scintillators or a failure of a circuit in reading all signals. The afterglow causes projection data of the N-th or subsequent projection to produce an afterimage, and causes a reconstructed image to contain artifacts. Since part of signals produced during the N-th projection is not read during the N-th projection, the number of signals acquired during the N-th projection is smaller than the number of true signals. When afterglow is compensated using output data of the (N+1)-th or subsequent projection, part of signals produced during the N-th projection which may become an outflow to the (N+1)-th or subsequent projection is estimated based on the N-th-projection output data with afterglow correction and the response characteristics of the detecting elements. If output data with afterglow correction disagrees with data represented by true signals, precision in afterglow correction is degraded.

Referring to FIG. 4, an example of processing to be performed by the central processor 105 shown in FIG. 2 will be described below. In the central processor 105, the characteristic of a detector measured in advance is stored in a detector characteristic memory means 303, and data corrected by the data correction means 301 is stored in a corrected data memory means 300. The data correction means 301 uses the stored data items to perform image correction on projection data transferred from the data acquisition means 118 to the central processor 105. Processing to be performed at this time includes offset correction during which a dark current component is removed from the output of the X-ray detector 104, afterglow correction during which an adverse effect of afterglow caused by the X-ray detector 104 is compensated, and sensitivity correction during which a distribution of irradiated X-rays or a variance of the sensitivities of X-ray detectors 104 is corrected. Projection data is subjected to convolution or back projection by a reconstruction means 302, whereby a tomographic image of an object expressing a distribution of X-ray absorption coefficients is produced. The tomographic image is displayed on the image display unit 106.

FIG. 1 shows an example of an afterglow correction method to be implemented by the data correction means 301 shown in FIG. 4. A description will be made of a case where afterglow correction is performed on N-th-projection projection data.

The data correction means 301 uses data 313 of a detector response characteristic, which is stored in the detector characteristic memory means 303, and projection data 320, which is stored in the corrected data memory means 300, produced during past projection, and has undergone afterglow correction, to produce data 312 of an afterglow amount that has occurred over past projections and becomes an inflow to the N-th projection. In FIG. 1, the data 312 of an afterglow amount is an afterglow amount which becomes an inflow to the N-th projection, whose adverse effect on a reconstructed image cannot be ignored, and which has occurred over m projections preceding the N-th projection. The data 312 of an afterglow amount occurring from the (N−m)-th projection to the (N−1)-th projection is calculated. The number of projections, m, is determined in advance. The data 312 of an afterglow amount having occurred over past projections is subtracted from the N-th-projection projection data 314 that is acquired by the data acquisition means 118 and that has not undergone afterglow correction, whereby the N-th-projection projection data 317 with afterglow correction (for past) is produced. Thus, afterglow that has occurred over past projections and becomes an inflow to the N-th projection is compensated.

Thereafter, the projection data 317 with afterglow correction (for past) and the data 313 of the response characteristic of a detector are used to calculate data 311 of an afterglow amount affecting future projections. Incidentally, n denotes the number of future projections during which a reconstructed image will undergo an adverse effect of an afterglow amount that cannot be ignored, and the n value is determined in advance. The n value is not identical to the m value. For example, when afterglow includes a long persisting component, past projections affecting the N-th projection are (N−1) projections starting with the first projection and ending with the (N−1)-th projection. The number of future projections may be larger than the number of (N−1) projections. Moreover, the future projections are projections during which data items may not be actually read. Consequently, the maximum n value may be an infinite. The calculated afterglow amount is added to the N-th-projection projection data 317 with afterglow correction (for past), whereby the N-th-projection projection data 315 with afterglow correction (for past and future) is worked out. Thus, signals to be left unread until the future projections succeeding the N-th projection due to afterglow can be obtained.

Consequently, the projection data 315 with afterglow correction (for past and future) is transferred to the reconstruction means 302.

Correction of an inflow from past projections and correction of an outflow to future projections are realized by, for example, the expression 6. Specifically, assuming that Lag(j) denotes the ratio of afterglow components having occurred over j projections which is calculated based on the data 313 of the response characteristic of a detector, I(N) denotes output data 314 produced during the N-th projection, and I'(N) denotes output data 315 produced by performing afterglow correction on the output data I(N), an adverse effect of the past projections is expressed as the second term of a numerator of the expression 1.

The value of the numerator of the expression 6 is expressed as follows:

$$\left(I(N) - \sum_{j=1}^{m}(Lag(j) \cdot I'(N-j))\right) \quad \text{[Expression 3]}$$

The value of the numerator corresponds to the N-th-projection output data 317 having an adverse effect of past projections compensated.

Assuming that part of signals left unread until future projections remains over n projections succeeding the N-th projection, an adverse effect of afterglow is expressed as a multiple of true signals, that is, the output data 315 I'(N) with afterglow correction as follows:

$$\sum_{j=1}^{n}(Lag(j)) \quad \text{[Expression 4]}$$

Consequently, when consideration is taken into part of signals left unread until future projections, true signals are expressed as a multiple of the numerator of the expression 6 as follows:

$$\left(1 \div \left(1 - \sum_{j=1}^{n}(Lag(j))\right)\right) \quad \text{[Expression 5]}$$

Through the calculation provided by the expression 6, correction of an inflow from past projections and correction of an outflow to future projections can be realized.

$$I'(N) = \frac{I(N) - \sum_{j=1}^{m}(Lag(j) \cdot I'(N-j))}{1 - \sum_{j=1}^{n}(Lag(j))} \quad \text{[Expression 6]}$$

FIG. 5 is an explanatory diagram concerning the ratio Lag(j) (where j denotes the number of projections succeeding X-ray irradiation) of afterglow components calculated based on the data 313 of the response characteristic of a detector shown in FIG. 1. The X-ray CT scanner in accordance with the present embodiment supports an afterglow measurement mode in which the data 313 of the response characteristic of a detector is produced. When the mode is selected, X-rays are impulsively irradiated for a short period of time. A change in an output value I(j) like the one shown in FIG. 5 is detected during each projection and stored in the detector characteristic memory means 303. Herein, a filled circle 200 denotes an output value calculated during projection. The value is used to calculate the Lag(j) value according to the expression 7.

$$Lag(j) = \frac{I(j)}{I(1)} \quad \text{[Expression 7]}$$

Owing to the foregoing configuration, there is provided an X-ray CT scanner capable of minimizing or removing artifacts in an image derived from afterglow caused by a detector, and highly precisely preventing degradation in a time resolution by performing data correction.

The present invention is not limited to the foregoing embodiment but is effectively adapted to an X-ray CT scanner including an X-ray detector that causes afterglow having a plurality of components. For example, the present invention is adapted to an X-ray CT scanner including an X-ray detector that converts X-rays directly into electric signals.

Second Embodiment

The second embodiment of the present invention is an X-ray CT scanner in which: afterglow is, unlike the first embodiment, estimated as the sum of components exhibiting different time constants and intensities; and the plurality of time constants and the plurality of intensities are stored as the values of the response characteristic 313 of a detector in the detector characteristic memory means 303. Referring to FIG. 6 to FIG. 9, the second embodiment of the present invention will be described below.

Figure 6:
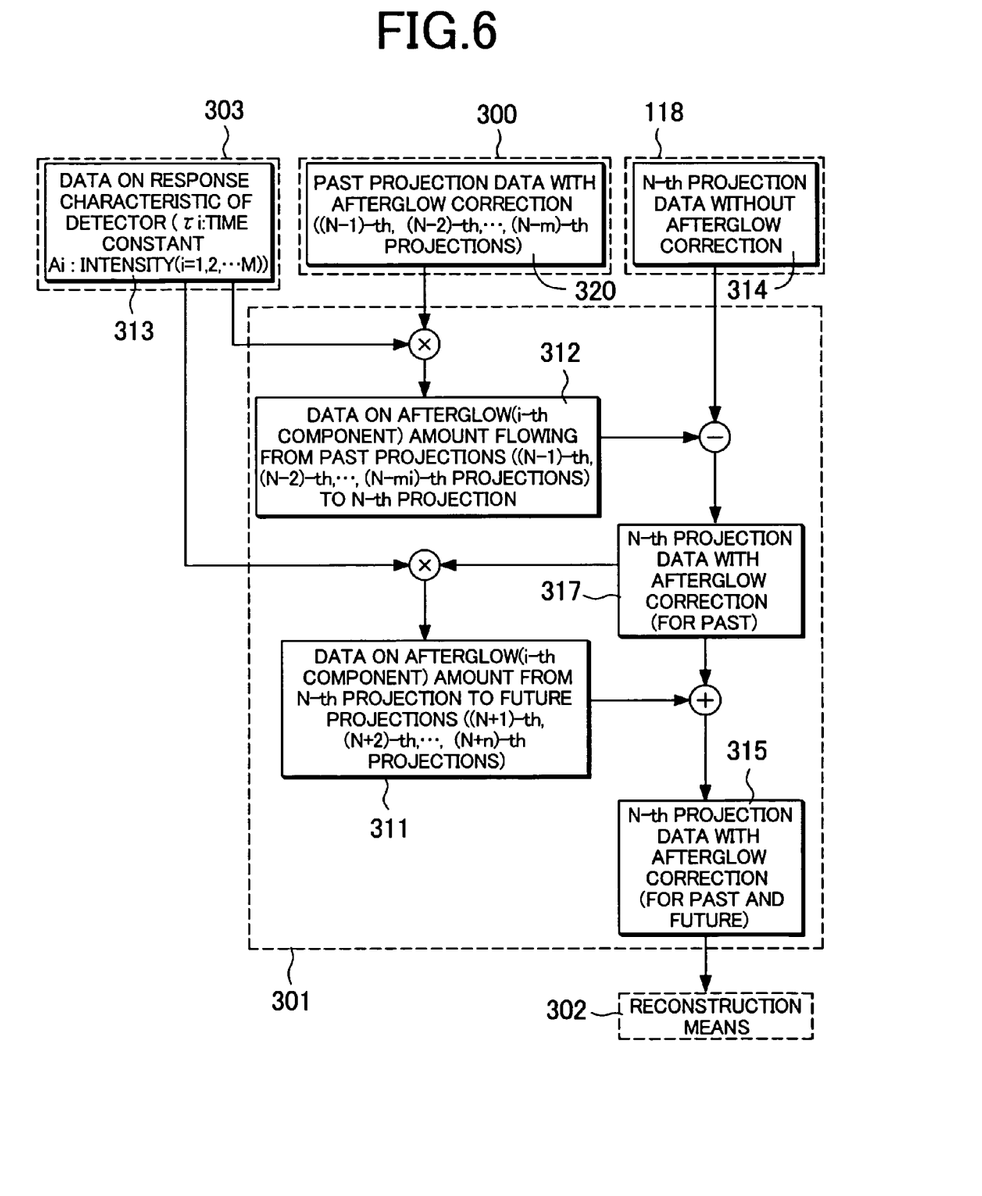
FIG. 6 is an explanatory diagram concerning an example of an afterglow correction method to be implemented by a data correction means included in the second embodiment of the present invention (second embodiment)
Figure 7:
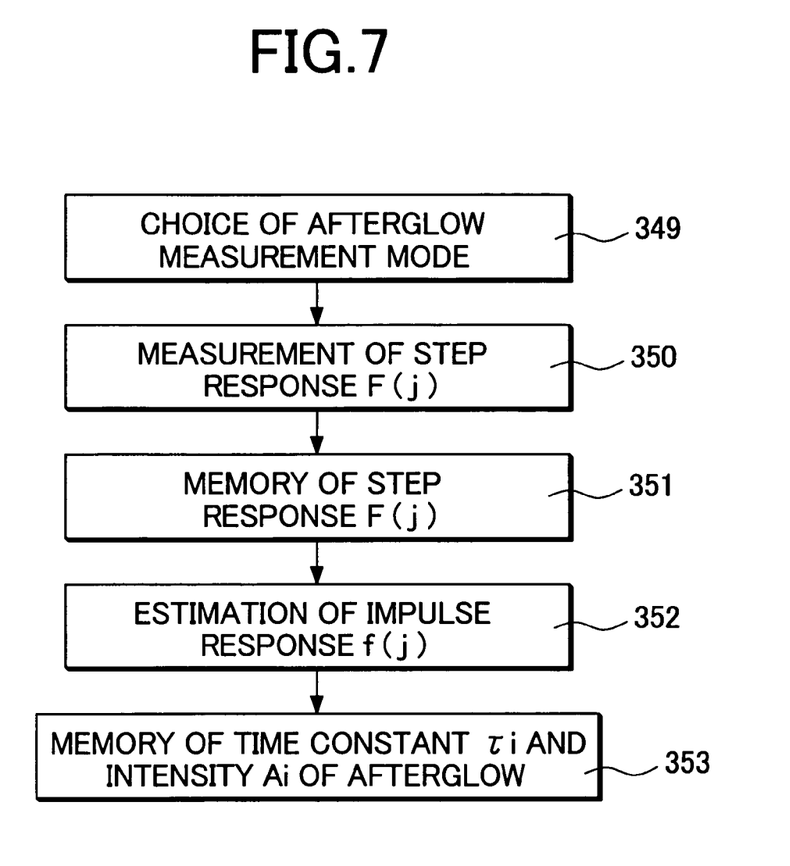
FIG. 7 is an explanatory diagram concerning an example of a method of determining a time constant and intensity of afterglow implemented in the second embodiment of the present invention (second embodiment)
Figure 8A:
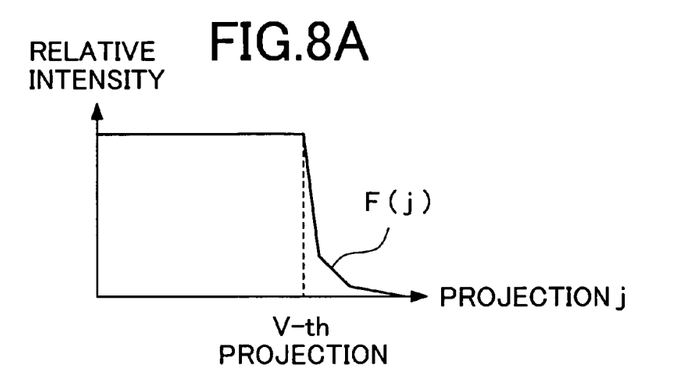
FIGS. 8A to 8C are explanatory diagrams concerning a step response characteristic to be measured and stored and an impulse response characteristic to be estimated which are employed in the method mentioned in FIG. 7 (second embodiment)
Figure 8B:
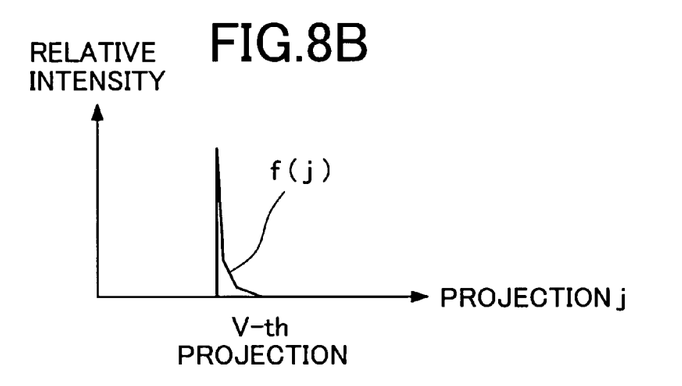
Figure 8C:
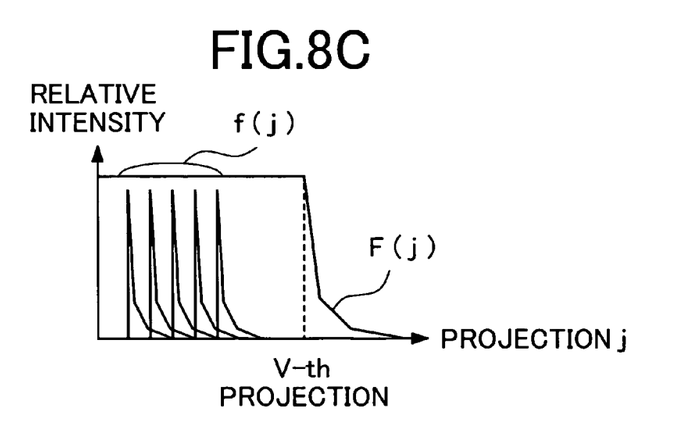
Figure 9A:
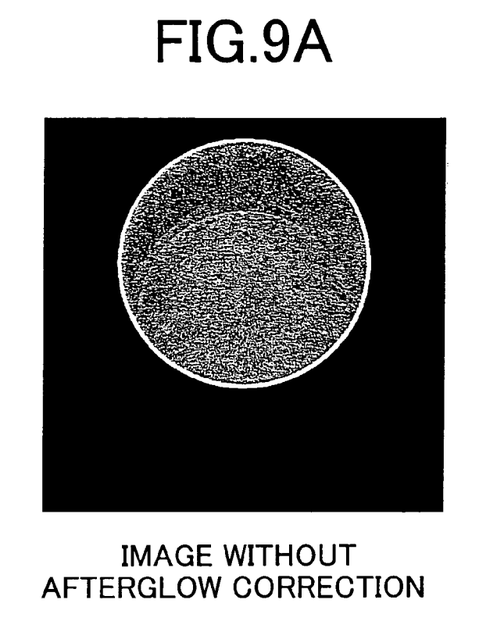
FIG. 9A shows a tomographic image produced without afterglow correction and FIG. 9B shows a tomographic image produced with afterglow correction.
Figure 9B:
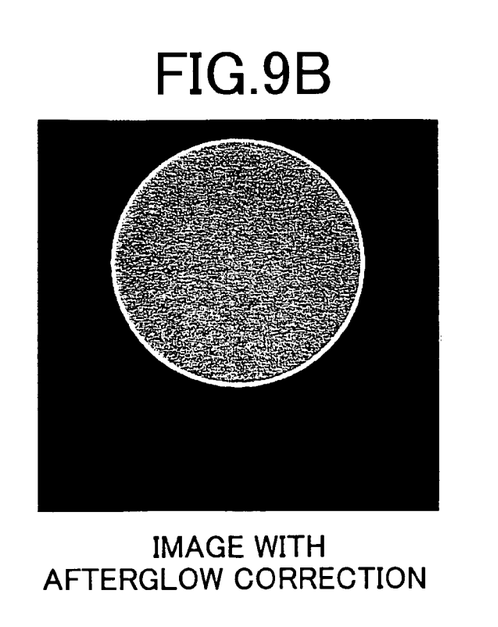

FIG. 6 is an explanatory diagram concerning another example of an afterglow correction method to be implemented by the data correction means shown in FIG. 4. FIG. 7 is an explanatory diagram concerning an example of a method of determining a time constant and intensity of afterglow. FIG. 8 is an explanatory diagram concerning a step response characteristic to be measured and stored as shown in FIG. 7, and an impulse response characteristic to be estimated. FIG. 9 shows a real image for explaining the advantages of the present invention.

As shown in FIG. 6, in the detector characteristic memory means 303, a time constant $\tau_i$ and intensity $A_i$ of an afterglow component i is stored as the data 313 of the response characteristic of a detector in relation to each X-ray detecting element. Herein, afterglow includes M components (i denotes 1, 2, etc., or M), and time constants $\tau_i$ and intensities $A_i$ of respective M components are stored.

The data correction means 301 uses the time constant $\tau_i$ and intensity $A_i$ of each afterglow component stored in the detector characteristic memory means 303 to calculate the data 312 of an afterglow amount having occurred over past projections. At this time, projection affected by an afterglow component varies depending on a time constant. A range m of projections affected by an inflow from past projections is determined in relation to each afterglow component i (herein, the m value determined in relation to each afterglow component shall be called an $m_i$ value). Likewise, a range n of projections causing an outflow to affect future projections is determined in relation to each afterglow component (herein, the n value determined in relation to each component shall be called an $n_i$ value). The data 311 of an afterglow amount affecting future projections is determined in relation to each afterglow component. Herein, the $m_i$ value and $n_i$ value are not always identical to each other.

Correction of an inflow from past projections and correction of an outflow to future projections are realized by an expression 8. In the expression 8, ΔT denotes a time interval between projections. The processing is performed relative to each X-ray detecting element.

$$I'(N) = \frac{I(N) - \sum_{i=1}^{M}\left(\sum_{j=1}^{mi}\left(A_i \exp\left(-\frac{j\Delta T}{\tau_i}\right)\cdot I'(N-j)\right)\right)}{1 - \sum_{i=1}^{M}\left(\sum_{j=1}^{ni}\left(A_i \exp\left(-\frac{j\Delta T}{\tau_i}\right)\right)\right)} \quad \text{[Expression 8]}$$

The data items 312, 311 of amounts of afterglow having occurred during past projections or affecting future projections, which are calculated for each afterglow component, are used to perform afterglow correction on the projection data 314. The corrected data 315 is transmitted to the reconstruction means 302.

Referring to FIG. 7, an example of a method of determining a time constant i and intensity $A_i$ of afterglow (where i denotes 1, etc., or M) will be described below. The determination is performed in the afterglow measurement mode. The procedure starts with choice 349 of the afterglow measurement mode in which general imaging cannot be performed. This is succeeded by measurement 350 of a step response characteristic F(j). The measurement 350 does not involve an object, but X-rays are irradiated for a certain period of time in order to detect the distribution of the values of the relative strength of an output of a detector. Incidentally, j denotes a projection number. This is succeeded by storage 351 of the step response characteristic F(j) in the detect or characteristic memory means 303.

The step response characteristic F(j) is plotted as a characteristic curve shown in FIG. 8A. FIG. 8A indicates the step response characteristic F(j) measured after X-rays are irradiated over the first to V-th projections. The step response characteristic F(j) is calculated by convoluting a step response characteristic f(j), which is detected during X-ray irradiation for the V-th projection alone as described in FIG. 8B, to each of impulse response characteristics f(j), which are detected over the first to V-th projections, and then integrating the resultant impulse response characteristics f(j) as FIG. 8C indicates.

As described in FIG. 7, the step response characteristic F(j) calculated through measurement 350 of the step response characteristics is stored in the corrected data memory means 300. The step response characteristic F(j) is used for estimation 352 of an impulse response characteristic f(j). In the estimation 352, for example, a fitting function F'(j) is obtained through convolution integral of impulse response functions f'(j) each of which is a function of the sum of afterglow components as provided by an expression 9 and which are detected over the first to V-th projections. The fitting function F(j) is fitted into a measured step function F(j) in order to estimate a time constant $\tau_i$ and intensity $A_i$ of afterglow (where i denotes 1, etc., or M).

$$f'(j) = \sum_{i=1}^{M} A_i \cdot \exp\left(-\frac{j\Delta T}{\tau_i}\right) \quad \text{[Expression 9]}$$

Herein, V may be set to 1 or any value larger than 1. When V is set to 1, it means that X-rays are irradiated impulsively.

The fitting function F'(j) becomes identical to the impulse response function f'(j). For the fitting, for example, the least squares method is employed. Thereafter, estimated parameters, that is, the time constant $\tau_i$ and intensity $A_i$ of afterglow (where i denotes 1, etc., or M) are stored for memory 353 in the corrected data memory means 300.

The estimation of the time constant $\tau_i$ and intensity $A_i$ of afterglow is performed in relation to each X-ray detecting element. At this time, not only the time constant $\tau_i$ and intensity $A_i$ but also the numbers of projections $m_i$ and $n_i$ and the number of afterglow components i may vary depending on the X-ray detecting element.

FIG. 9 shows tomographic images actually produced by the X-ray CT scanner. A cylindrical phantom being filled with water and having a diameter of 305 mm is adopted as an object. FIG. 9A shows the tomographic image produced without afterglow correction, and FIG. 9B shows the tomographic image produced with the afterglow correction. In the afterglow correction resulting in the image shown in FIG. 9B, five afterglow components (M=5) are taken for instance, and the time constant $\tau_i$ and intensity $A_i$ of afterglow are determined relative to each pixel. The numbers of projections $m_i$ and $n_i$ are set to values required for each afterglow component to occupy one-one hundred millionth of an input signal. However, the $m_i$ value should not exceed the range of projections.

If the afterglow correction is not performed as shown in FIG. 9A, ring artifacts occur. In contrast, if the afterglow correction is performed as shown in FIG. 9B, the number of artifacts is minimized. This verifies the advantage of the present invention in minimizing artifacts.

In the X-ray CT scanner according to the second embodiment, compared with the X-ray CT scanner according to the first embodiment, even when afterglow contains a component whose time constant is long, the amount of data 313 of the response characteristic of a detector stored in the detector characteristic memory means 303 is small. The ratio Lag(i) of afterglow components can be highly precisely determined through fitting. The range of projections, $m_i$, which are affected by an inflow from past projections due to respective afterglow components, and the range of projections, $n_i$, which cause an outflow to affect future projections can be determined. This provides the merit that the number of calculations is decreased and processing is speeded up.

Moreover, the present invention is not limited to the aforesaid embodiments but can be varied in various manners without a departure from the gist. Furthermore, the aforesaid embodiments each include various stages, and various embodiments are conceivable by combining the disclosed constituent features. For example, some of the constituent features of the embodiment may be excluded.

As described so far, according to the present invention, there is provided an X-ray CT scanner capable of compensating not only an inflow of signals from past projections but also an outflow of signals to future projections so as to highly precisely reproduce true signals produced during current projection. Moreover, the X-ray CT scanner can prevent degradation in a spatial resolution occurring in a reconstructed image due to afterglow and/or deterioration in image quality derived from occurrence of artifacts.

INDUSTRIAL APPLICABILITY

The present invention realizes an X-ray CT scanner capable of minimizing or removing artifacts in an image derived from afterglow caused by an X-ray-detector, and highly precisely preventing degradation in a time resolution by performing data correction. The present invention will be highly efficiently applied to the field of medicine.

The invention claimed is:

1. An X-ray CT scanner including an X-ray source that irradiates X-rays to an object, an X-ray detector composed of a plurality of X-ray detecting elements which convert X-rays penetrating the object into electric signals at every timing of projection, a data correction means for correcting an output of the X-ray detector, and an arithmetic processing means for performing arithmetic processing on an output of the data correction means so as to reconstruct an image, comprising:

a first memory means in which data of the response characteristic of the X-ray detector that is the afterglow-related characteristic thereof and that is measured in advance is stored; and a second memory means in which output data items produced by the X-ray detector over past projections and corrected by the data correction means on the basis of the response characteristic data are stored, wherein:

the data correction means includes an afterglow correction means that uses the response characteristic data stored in the first memory means and the plurality of output data items, which are produced over a plurality of past projections and stored in the second memory means, to compensate both an adverse effect of inflow of signals from the past projections due to afterglow on output data producing current projection, and an adverse effect of outflow of signals to future projections.

2. The X-ray CT scanner according to claim 1, wherein the X-ray CT scanner supports an afterglow measurement mode in which X-rays are impulsively irradiated only during projection or stepwise irradiated only during a plurality of projections in order to acquire in advance data of the response characteristic of the X-ray detector that is the afterglow-related characteristic thereof, and includes a facility for selecting the afterglow measurement mode.

3. An X-ray CT scanner including an X-ray source that irradiates X-rays to an object, an X-ray detector composed of a plurality of X-ray detecting elements which convert X-rays penetrating the object into electric signals, a data correction means for correcting an output of the X-ray detector, and an arithmetic processing means for performing arithmetic processing on an output of the data correction means so as to reconstruct an image, comprising:

a first memory means in which data of the response characteristic of the X-ray detector that is the afterglow-related characteristic thereof and that is measured in advance is stored; and a second memory means in which output data items produced by the X-ray detector over past projections and corrected by the data correction means on the basis of the response characteristic data are stored, wherein:

the data correction means includes an afterglow correction means that uses the response characteristic data stored in the first memory means and the output data items, which are produced over the past projections and stored in the second memory means, to compensate both an adverse effect of inflow of signals from the past projections due to afterglow on output data produced during current projection, and an adverse effect of outflow of signals to future projections according to a predetermined expression;

assuming that Lag(j) denotes the ratio of afterglow components that have occurred over j projections since the irradiated X-rays fall on the X-ray detector, m denotes the number of past projections over which afterglow components to be compensated have occurred since the X-rays fall on the X-ray detector, n denotes the number of future projections for which an afterglow component having occurred since the X-rays fall on the X-ray detector should be compensated, I(N) denotes output data produced after N projections have been completed since the X-rays fall on the X-ray detector, and I'(N) denotes output data produced when the data correction means corrects the output data I(N), which is produced after the completion of N projections, so as to compensate the afterglow, the predetermined expression is provided as follows:

$$I'(N) = \frac{I(N) - \sum_{j=1}^{m}(Lag(j) \cdot I'(N-j))}{1 - \sum_{j=1}^{n}(Lag(j))}.$$

4. The X-ray CT scanner according to claim 3, wherein:
the response characteristic of the X-ray detector is indicated by the sum of afterglow components exhibiting different time constants and intensities;
the number of past projections, m, over which afterglow components to be compensated have occurred and/or the number of future projections, n, for which an afterglow component having occurred since the X-rays fall on the X-ray detector should be compensated vary depending on the afterglow component.

5. The X-ray CT scanner according to claim 3, wherein the X-ray CT scanner supports an afterglow measurement mode in which X-rays are impulsively irradiated only during projection or stepwise irradiated only during a plurality of projections in order to acquire in advance data of the response characteristic of the X-ray detector that is the afterglow-related characteristic thereof, and includes a facility for selecting the afterglow measurement mode.

6. An X-ray CT scanner including an X-ray source that irradiates X-rays to an object, an X-ray detector composed of a plurality of X-ray detecting elements which convert X-rays penetrating the object into electric signals, a data correction means for correcting an output of the X-ray detector, and an arithmetic processing means for performing arithmetic processing on an output of the data correction means so as to reconstruct an image, comprising:
a first memory means in which time constants and intensities of afterglow including a plurality of predetermined components are stored; and
a second memory means in which output data items produced by the X-ray detector over past projections and corrected by the data correction means on the basis of the time constants and intensities of the afterglow components are stored, wherein:
the data correction means includes an afterglow correction means that uses the time constants and intensities of the respective afterglow components stored in the first memory means and the output data items, which are produced over the past projections and stored in the second memory means, to compensate, according to a predetermined expression, both an adverse effect of inflow of signals from the past projections due to the afterglow on output data produced during current projection, and an adverse effect of outflow of signals to future projections; and
assuming that $\Delta T$ denotes a time interval between projections, M denotes the number of afterglow components, $\tau_i$ denotes a time constant of an afterglow component i (where i denotes 1, 2, etc., or M), $A_i$ denotes an intensity of the afterglow component i, $m_i$ denotes the number of past projections over which the afterglow components i to be compensated have occurred since the X-rays fall on the X-ray detector, $n_i$ denotes the number of future projections for which an afterglow component i having occurred since the X-rays fall on the X-ray detector should be compensated, I(N) denotes output data produced when N projections have been completed since the X-rays fall on the X-ray detector, and I'(N) denotes output data produced when the data correction means corrects the output data I(N), which is produced after the completion of N projections, so as to compensate the afterglow, the predetermined expression is provided as follows:

$$I'(N) = \frac{I(N) - \sum_{i=1}^{M}\left[\sum_{j=1}^{mi}\left(A_i \exp\left(-\frac{j\Delta T}{\tau_i}\right) \cdot I'(N-j)\right)\right]}{1 - \sum_{i=1}^{M}\left[\sum_{j=1}^{ni}\left(A_i \exp\left(-\frac{j\Delta T}{\tau_i}\right)\right)\right]}.$$

7. The X-ray CT scanner according to claim 6, wherein the X-ray CT scanner supports an afterglow measurement mode in which X-rays are impulsively irradiated only during projection or stepwise irradiated only during a plurality of projections in order to acquire in advance data of the response characteristic of the X-ray detector that is the afterglow-related characteristic thereof, and includes a facility for selecting the afterglow measurement mode.

* * * * *